(12) United States Patent
Clark

(10) Patent No.: US 6,172,054 B1
(45) Date of Patent: *Jan. 9, 2001

(54) COMBINATION THERAPY FOR LOWERING AND CONTROLLING INTRAOCULAR PRESSURE

(75) Inventor: Abbot F. Clark, Arlington, TX (US)

(73) Assignee: Alcon Laboratories, Inc., Fort Worth, TX (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/491,005

(22) Filed: Jun. 15, 1995

(51) Int. Cl.⁷ .................................................. A61K 31/56
(52) U.S. Cl. ........................ 514/179; 514/172; 514/173; 514/176; 514/180; 514/182; 514/913
(58) Field of Search .................................. 514/172, 173, 514/176, 179, 180, 182, 913

(56) References Cited

U.S. PATENT DOCUMENTS

| | | | |
|---|---|---|---|
| 4,540,408 | 9/1985 | Lloyd | 604/294 |
| 4,599,353 | 7/1986 | Bito | 514/530 |
| 4,730,013 | 3/1988 | Bondi et al. | 524/42 |
| 4,797,413 | 1/1989 | Baldwin et al. | 514/432 |
| 4,861,760 | 8/1989 | Mazuel et al. | 514/54 |
| 4,876,250 | 10/1989 | Clark | 514/179 |
| 4,911,920 | 3/1990 | Jani et al. | 424/78 |
| 5,093,329 | 3/1992 | Woodward | 514/469 |
| 5,153,192 | 10/1992 | Dean et al. | 514/226.5 |
| 5,212,162 | 5/1993 | Missel et al. | 514/54 |
| 5,240,923 | 8/1993 | Dean et al. | 514/226.5 |
| 5,321,128 | 6/1994 | Stjernschantz et al. | 514/530 |
| 5,371,078 | 12/1994 | Clark et al. | 514/182 |
| 5,378,703 | 1/1995 | Dean et al. | 514/222.8 |
| 5,403,841 | 4/1995 | Lang et al. | 514/226.8 |

OTHER PUBLICATIONS

*Pediat. Neurosci.*, Knepper, et al., vol. 12, pp. 240–251 (1985–86), *Glycosaminoglycans and Outflow Pathways of the Eye and Brain.*

*Endocrinology*, Ingber, et al., 119:1768–1775 (1986), *A Possible Mechanism for Inhibition of Angiogenesis by Angiostatic Steroids: Induction of Capillary Basement Membrane Dissolution.*

Clark et al., IOVS 35 (Suppl.): 1057, 1994.

*Ophthalmology*, Rohen, Johannes W., vol. 90, No. 7 (Jul., 1983), *Why is Intraocular Pressure Elevated in Chronic Simple Glaucoma?*

*Mayo Clin. Proc.*, Johnson, et al., vol. 61, pp. 59–67 (Jan., 1986), *Glaucoma: An Overview.*

*Primary Examiner*—Zohreh Fay
(74) *Attorney, Agent, or Firm*—Sally Yeager

(57) ABSTRACT

Angiostatic agents and another IOP lowering compound are combined in ophthalmic compositions to treat glaucoma and ocular hypertension. Methods for treating glaucoma and ocular hypertension are also disclosed.

16 Claims, No Drawings

COMBINATION THERAPY FOR LOWERING AND CONTROLLING INTRAOCULAR PRESSURE

The present invention relates generally to the field of ophthalmology. In particular, the invention relates to the treatment of glaucoma using a combination of an angiostatic agent which lowers intraocular pressure (IOP) and a second IOP lowering compound.

BACKGROUND OF THE INVENTION

Although the underlying causes of glaucoma are not understood at this time, glaucoma is characterized by damage to the optic nerve, accompanied by a decrease in the normal visual field. One early warning sign of possible glaucomatous visual field loss is elevated IOP.

There are angiostatic agents which are known to lower IOP, see, for example, U.S. Pat. Nos. 4,876,250 and 5,371,078. These compounds are very effective in controlling ocular hypertension, but they usually exhibit a slow onset of action; that is, it can take several weeks before an IOP lowering effect is seen.

Other known IOP controlling agents, such as miotics, sympathomemetics, beta-blockers, carbonic anhydrase inhibitors, and prostaglandins are immediately effective in lowering IOP.

The compositions of the present invention contain an angiostatic agent which provides effective, long duration control of IOP and a second IOP lowering compound to provide immediate control of a patient's elevated IOP. This combination is more effective in that a patient's IOP can be lowered and controlled with less IOP spiking. In addition, the effectiveness of the combination is at least additive because the angiostatic agents lower IOP via a different mechanism than any of the second IOP lowering compounds described in this invention.

SUMMARY OF THE INVENTION

The present invention is directed to compositions useful in the treatment of glaucoma and ocular hypertension. The compositions contain a combination of at least one angiostatic agent and at least one other compound which lowers IOP ("second agent"). The compositions are used to lower and control IOP by topical application to a patient's affected eye(s).

DETAILED DESCRIPTION OF THE INVENTION

The development of blood vessels for the purpose of sustaining viable tissue is known as angiogenesis or neovascularization. Agents which inhibit neovascularization are known by a variety of terms such as angiostatic, angiolytic, or angiotropic agents. In addition, it has been demonstrated that many angiostatic agents have significant IOP lowering activity, Clark et al., IOVS 35 (Suppl.): 1057, 1994. For purposes of this specification, the term "angiostatic agent" means compounds which inhibit new blood vessel formation as well as lower and/or control intraocular pressure associated with glaucoma or ocular hypertension.

Without intending to be bound by any theory, it is believed that angiostatic agents act to control intraocular pressure by inhibiting the accumulation or stimulating the dissolution of amorphous extracellular material in the trabecular meshwork of the eye. The presence of this amorphous extracellular material alters the integrity of the healthy trabecular meshwork and is a symptom associated with primary open angle glaucoma (POAG). It is not well understood why this amorphous extracellular material builds up in the trabecular meshwork of persons suffering from POAG. However, it has been found that the amorphous extracellular material is generally composed of glycosaminoglycans (GAGs) and basement membrane material; see, Ophthalmology, Vol.90, No.7 (July 1983); *Mayo Clin. Proc*, Vol.61, pp.59–67 (Jan.1986); and *Pediat. Neurosci.* Vol.12, pp.240–251 (1985–86). When these materials build up in the trabecular meshwork, the aqueous humor, normally present in the anterior chamber of the eye, cannot leave this chamber through its normal route (the trabecular meshwork) at its normal rate. Therefore, a normal volume of aqueous humor is produced by the ciliary processes of the eye and introduced into the anterior chamber, but its exit through the trabecular meshwork is abnormally slow. This results in a buildup of pressure in the eye, ocular hypertension, which can translate into pressure on the optic nerve. The ocular hypertension so generated can lead to blindness due to damage to the optic nerve.

It is believed that the angiostatic agents function in the trabecular meshwork in a similar manner as shown by Ingber, et al., wherein it was shown that angiostatic steroids caused dissolution of the basement membrane scaffolding using a chick embryo neovascularization model; *Endocrinology*, 119, pp.1768–1775 (1986). It is believed that angiostatic agents prevent the accumulation, or promote the dissolution of, amorphous extracellular materials in the trabecular meshwork by inhibiting the formation of basement membrane materials and glycosaminoglycans. Thus, by preventing the development of these materials or promoting their dissolution, the normal integrity of the trabecular meshwork is retained and aqueous humor may flow through the trabecular meshwork at normal rates. As a result, the intraocular pressure of the eye is controlled.

Preferred angiostatic agents are represented by the following structures:

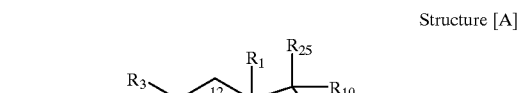

Structure [A]

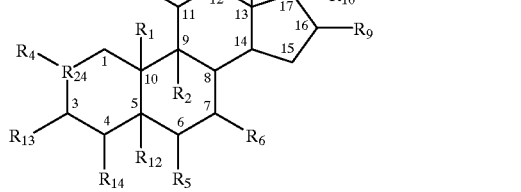

Structure [B]

wherein $R_1$ is H, β—$CH_3$ or β—$C_2H_5$;
$R_2$ is F, $C_9$–$C_{11}$ double bond, $C_9$–$C_{11}$ epoxy, H or Cl;
$R_3$ is H, $OR_{26}$, $OC(=O)R_{27}$, halogen, $C_9$–$C_{11}$ double bond, $C_9$–Cl, epoxy, =O, —OH, —O— alkyl($C_1$-$C_{12}$), —OC(=O)alkyl($C_1$-$C_{12}$), —OC(=O)ARYL, —OC(=O)N (R)$_2$ or —OC(=O)OR$_7$, wherein ARYL is furyl, thienyl, pyrrolyl, or pyridyl and each of said moieties is optionally substituted with one or two (C$_1$–C$_4$)alkyl groups, or ARYL is —(CH$_2$)$_f$-phenyl wherein f is 0 to 2 and the phenyl ring is optionally substituted with 1 to 3 groups selected from chlorine, fluorine, bromine, alkyl(C$_1$–C$_3$), alkoxy(C$_1$–C$_3$), thioalkoxy-(C$_1$–C$_3$), Cl$_3$C—, F$_3$C—, —NH$_2$ and —NHCOCH$_3$ and R is hydrogen, alkyl (C$_1$–C$_4$), or phenyl and each R can be the same or different, and R$_7$ is ARYL as herein defined, or alkyl (C$_1$–C$_{12}$);

R$_4$ is H, CH$_3$, Cl or F;

R$_5$ is H, OH, F, Cl, Br, CH$_3$, phenyl, vinyl or allyl;

R$_6$ is H or CH$_3$;

R$_9$ is CH$_2$CH$_2$OR$_{26}$, CH$_2$CH$_2$OC(=O)R$_{27}$, H, OH, CH$_3$, F, =CH$_2$, CH$_2$C(=O)OR$_{28}$, OR$_{26}$, O(C=O)R$_{27}$ or O(C=O)CH$_2$(C=O)OR$_{26}$

R$_{10}$ is —C≡CH, —CH=CH$_2$, halogen, CN, N$_3$, OR$_{26}$, OC(=O)R$_{27}$, H, OH, CH$_3$ or R$_{10}$ forms a second bond between positions C-16 and C-17;

R$_{12}$ is H or forms a double bond with R$_1$ or R$_{14}$;

R$_{13}$ is halogen, OR$_{26}$, OC(=O)R$_{27}$, NH$_2$, NHR$_{26}$, NHC(=O)R$_{27}$, N(R$_{26}$)$_2$, NC(=O)R$_{27}$, N$_3$, H, —OH, =O, —O—P(=O)(OH)$_2$, or —O—C(=O)—(CH$_2$)$_t$COOH where t is an integer from 2 to 6;

R$_{14}$ is H or forms a double bond with R$_{12}$;

R$_{15}$ is H, =O or —OH;

and R$_{23}$ with R$_{10}$ forms a cyclic phosphate;

wherein R$_9$ and R$_{15}$ have the meaning defined above;

or wherein R$_{23}$ is —OH, O—C(=O)—R$_{11}$, —OP(O)—(OH)$_2$, or —O—C(=O)—(CH$_2$)$_t$COOH wherein t is an integer from 2 to 6; and R$_{11}$ is —Y—(CH$_2$)$_n$—X—(CH$_2$)$_m$—SO$_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond, —CON(R$_{18}$)—, —N(R$_{18}$)CO—, —O—, —S—, —S(O)—, or —S(O$_2$)—; R$_{18}$ is hydrogen or alkyl (C$_1$-C$_4$); each of R$_{16}$ and R$_{17}$ is a lower alkyl group of from 1 to 4 carbon atoms optionally substituted with one hydroxyl or R$_{16}$ and R$_{17}$ taken together with the nitrogen atom to which each is attached forms a monocydic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —R$_{19}$—CH$_2$COOH wherein R$_{19}$ is —S—, —S(O)—, —S(O)$_2$—, —SO$_2$N(R$_{20}$)—, or N(R$_{20}$)SO$_2$—; and R$_{20}$ is hydrogen or lower alkyl-(C$_1$–C$_4$); with the proviso that the total number of carbon atoms in R$_{20}$ and (CH$_2$)$_r$ is not greater than 10; or (2) —CO—COOH; or (3) CON(R$_{21}$)CH(R$_{22}$)COOH wherein R$_{21}$ is H and R$_{22}$ is H, CH$_3$, —CH$_2$COOH, —CH$_2$CH$_2$COOH, —CH$_2$OH, —CH$_2$SH, —CH$_2$CH$_2$SCH$_3$, or —CH$_2$Ph—OH wherein Ph—OH is phydroxyphenyl;

or R$_{21}$ is CH$_3$ and R$_{22}$ is H;

or R$_{21}$ and R$_{22}$ taken together are —CH$_2$CH$_2$CH$_2$—;

or —N(R$_{21}$)CH(R$_{22}$)COOH taken together is —NHCH$_2$CONHCH$_2$COOH; and pharmaceutically acceptable salts thereof;

R$_{24}$=C, C$_1$–C$_2$ double bond, O;

R$_{25}$=C(R$_{15}$)CH$_2$—R$_{23}$, OH, OR$_{26}$, OC(=O)R$_{27}$, R$_{26}$, COOH, C(=O)OR$_{26}$, CHOHCH$_2$OH, CHOHCH$_2$OR$_{26}$, CHOHCH$_2$OC(=O)R$_{27}$, CH$_2$CH$_2$OHCH$_2$CH$_2$OR$_{26}$, CH$_2$CH$_2$OC(=O)R$_{27}$, CH$_2$CN, CH$_2$N$_3$, CH$_2$NH$_2$, CH$_2$NHR$_{26}$, CH$_2$N(R$_{26}$)$_2$, CH$_2$OH, CH$_2$OR$_{26}$, CH$_2$O(C=O)R$_{27}$, CH$_2$O(P=O) (OH)$_2$, CH$_2$O(P=O) (OR$_{26}$)$_2$, CH$_2$SH, CH$_2$S—R$_{26}$, CH$_2$SC(=O)R$_{27}$, CH$_2$NC(=O)R$_{27}$, C(=O)CHR$_{28}$OH, C(=O)CHR$_{28}$OR$_{26}$, C(=O)CHR$_{28}$OC(=O)R$_{27}$ or R$_{10}$ and R$_{25}$ taken together may be =C(R$_{28}$)$_2$, that is, an optionally alkyl substituted methylene group;

wherein R$_{26}$=C$_1$–C$_6$ (alkyl, branched alkyl, cydoalkyl, haloalkyl, aralkyl, aryl);

R$_{27}$=R$_{26}$+OR$_{26}$; R$_{28}$=H, C1–C6 (alkyl, branched alkyl, cycloalkyl).

The other IOP-lowering compounds useful in the present invention, second agents, include all presently known IOP-lowering compounds, including miotics (e.g., pilocarpine, carbachol and acetylcholinesterase inhibitors); sympathomimetics (e.g., epinephrine, dipivalylepinephrine and para-amino donidine); beta-blockers (e.g., betaxolol, levobunolol, carteolol, and timolol); prostaglandins and their analogues and derivatives (e.g., F series (such as PGF$_{2\alpha}$), E series (such as PGE$_2$), D series (such as PGD$_2$) and compounds disclosed in U.S. Pat. Nos. 4,599,353; 5,093,329; and 5,321,128, and in European Patent Nos. 0215 860 B1 and 0 299 914 B1; and carbonic anhydrase inhibitors (e.g., acetazolamide, methazolamide, and ethoxzolamide, and compounds disclosed in U.S. Pat. Nos. 5,153,192; 5,240,923; 5,378,703; and 4,797,413). The preferred IOP-lowering compounds are: timolol, betaxolol, levobunolol, carteolol, pilocarpine, carbachol, epinephrine, dipivalyl epinephrine, -methyl dipivalylepinephrine, Trusopt, latanoprost, apradonidine, and donidine.

The compositions contain an amount of an angiostatic agent between 0.0001 and 10.0 percent by weight (wt %) and an amount of a second agent between 0.00001 and 10.0 wt %. Preferably, the angiostatic agent concentration is between 0.001 and 5.0 wt %, especially preferred are concentrations between 0.01 and 2.5 wt %. The second agent concentration is preferably between 0.001 and 5.0 wt %, 0.01 to 2.5 wt % is especially preferred.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference.

As used herein, the term "finely-divided drug carrier substrate" (or "DCS") means finely-divided solids, colloidal particles, or soluble polymers and/or polyelectrolytes which are capable of selective adsorption or binding with drug molecules. Examples of DCS include, but are not limited to: finely divided silica, such as fumed silica, silicates, and bentonites; ion exchange resins, which can be anionic, cationic, or non-ionic in nature; and soluble polymers, such as, alginic acid, pectin, soluble carrageenans, Carbopol®, and polystyrene sulfonic acid. In general, the DCS component is used at a level in the range of about 0.05 to about 10.0 wt %. For particulate DCS, the average particle size diameter ranges from 1 to 20 microns. The amount of DCS and its characteristics (e.g., amount of cross-linking, particle size) may be varied in order to produce the desired time-release profile for the chosen drug.

In addition to the above-described principal ingredients, the anti-glaucoma compositions of the present invention may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, Onamer M® and other agents equally well-known to those skilled in the art. Such preservatives, if utilized, will typically be employed in an amount between about 0.001 and about 1.0 wt %. Examples of suitable agents which may be used to adjust the tonicity or osmolality of the formulations include: sodium chloride, potassium chloride, mannitol, dextrose, glycerin, and propylene glycol. Such agents, if utilized, will typically be employed in an amount between about 0.1 and about 10.0 wt %.

As will be appreciated by those skilled in the art, the compositions may be formulated in various dosage forms suitable for topical ophthalmic delivery, including solutions, suspensions, emulsions, gels, and erodible solid ocular inserts. The compositions are preferably aqueous suspensions or solutions.

The compositions of the present invention may also comprise non-aqueous formulations such as: substantially non-aqueous liquids substantially non-aqueous semi-solid compositions and solid compositions or devices.

The first class, substantially non-aqueous liquids, comprise an angiostatic agent and a second agent ("drug combination") dissolved or suspended in one or more of the following: vegetable and mineral oils, such as, liquid petrolatum, corn oil, castor oil, sesame oil, and peanut oil; triglycerides, such as the capric/caprylic triglycerides commonly used in foods and cosmetics; liquid lanolin and lanolin derivatives; and perfluorohydrocarbons.

The second class, semi-solid compositions, comprise a drug combination dissolved or suspended in one or more of the following: various types of petrolatum, such as white, yellow, red and so on; lanolin and lanolin derivatives; gelled mineral oil having a hydrocarbon base, such as Plastibase®; petrolatum and ethylene carbonate mixtures; petrolatum in combination with surfactants and polyglycol, such as polyoxyl 40 stearate and polyethylene glycol.

The third class, solid compositions or devices, include non-erodible devices which are inserted into the conjunctival sac of the eye and later removed, such as the Alza-type diffusion or osmotic pressure controlled polymer membranes; and bioerodible polymers which do not have to be removed from the conjunctival sac, such as essentially anhydrous but water soluble polymers and resins (e.g., celluloses, polycarboxylic acids, and so on). Especially preferred are the bioerodible inserts described and detailed in U.S. Pat. No. 4,540,408 (Lloyd) and U.S. Pat. No. 4,730,013 (Bondi et al.), wherein drug combinations of the present invention would be entrained in a non-aqueous matrix consisting essentially of polyvinyl alcohol. The entire contents of these two patents are incorporated herein by reference.

The present invention is also directed to methods of treating glaucoma and ocular hypertension. The compositions described above are applied topically to the affected eye(s) of the patient. The frequency and amount of dosage will be determined by the clinician based on various clinical factors. The methods will typically comprise topical application of one or two drops (or an equivalent amount of a solid or semi-solid dosage form) to the affected eye one to four times per day.

The following examples are illustrative of compositions of the present inventions. Example 2 represents the preferred combination.

EXAMPLE 1

| Ingredient | wt. % |
|---|---|
| Apraclonidine HCl | 0.58 |
| 5β-Pregnane-3α,11β,17α, 21-tetrol-20-one (Tetrahydrocortisol) | 1.0 |
| Tyloxapol | 0.01 to 0.05 |
| Hydroxy Propyl Methylcellulose | 0.5 |
| Benzalkonium Chloride | 0.01 |
| Sodium Chloride | 0.8 |
| Edetate Disodium | 0.01 |
| NaOH/HCl | q.s. pH 7.4 |
| Purified Water | q.s. 100 mL |

EXAMPLE 2

| Ingredient | wt. % |
|---|---|
| Timolol Maleate | 0.68 |
| 4,9(11)Pregnadien-17α, 21-diol-3;20-dione-21-acetate | 1.0 |
| Mannitol | 2.4 |
| Sodium Chloride | 0.4 |
| Carbopol 974P | 0.5 |
| Polysorbate 80 | 0.05 |
| Edetate disodium | 0.01 |
| Benzalkonium chloride | 0.01 |
| NaOH | q.s. pH 7.4 |
| Purified Water | q.s. 100 mL |

EXAMPLE 3

| Ingredient | wt. % |
|---|---|
| Betaxolol HCl | 0.28 |
| 17α-Ethynyl estradiol | 1.00 |
| Benzalkonium Chloride | 0.01 |
| Mannitol | 4.50 |
| Amberlite IRP-69 | 0.25 |
| Carbomer 934P | 0.20 |
| Edetate disodium | 0.01 |
| HCl/NaOH | q.s. pH 7.6 |
| Purified Water | q.s. 100 mL |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

I claim:

1. A composition for lowering IOP and controlling IOP spiking comprising a pharmaceutically effective amount of an angiostatic agent with the structure Structure [A]

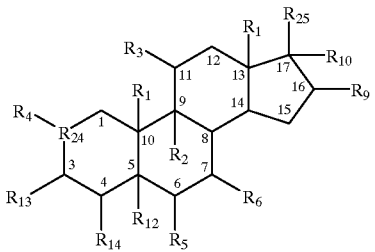

Structure [B]

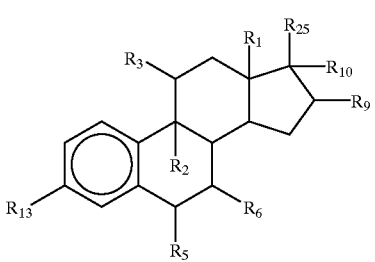

wherein $R_1$ is H, $\beta$—$CH_3$ or $\beta$—$C_2H_5$;

$R_2$ is F, $C_9$-$C_{11}$, double bond, $C_9$-$C_{11}$1 epoxy, H or Cl;

$R_3$ is H, $OR_{26}$, $OC(=O)R_{27}$, halogen, $C_9$-$C_{11}$ double bond, $C_9$-Cl, epoxy, =O, —OH, —O— alkyl ($C_1$-$C_{12}$), —OC(=O)alkyl($C_1$-$C_{12}$), —OC(=O)ARYL, —OC(=O)N(R)$_2$ or —OC(=O)OR$_7$, wherein ARYL is furyl, thienyl, pyrrolyl, or pyridyl and each of said moieties is optionally substituted with one or two ($C_1$-$C_4$)alkyl groups, or ARYL is —($CH_2$)$_f$-phenyl wherein f is 0 to 2 and the phenyl ring is optionally substituted with 1 to 3 groups selected from chlorine, fluorine, bromine, alkyl($C_1$-$C_3$), alkoxy($C_1$-$C_3$), thioalkoxy-($C_1$-$C_3$), $Cl_3C$—, $F_3C$—, —$NH_2$ and —$NHCOCH_3$ and R is hydrogen, alkyl ($C_1$-$C_4$), or phenyl and each R can be the same or different, and $R_7$ is ARYL as herein defined, or alkyl($C_1$-$C_{12}$);

$R_4$ is H, $CH_3$, Cl or F;

$R_5$ is H, OH, F, Cl, Br, $CH_3$, phenyl, vinyl or allyl;

$R_6$ is H or $CH_3$;

$R_9$ is $CH_2CH_2OR_{26}$, $CH_2CH_2OC(=O)R_{27}$, H, OH, $CH_3$, F, =$CH_2$, $CH_2C(=O)OR_{28}$, $OR_{26}$, $O(C=O)R_{27}$ or $O(C=O)CH_2C(=O)OR_{26}$ $R_{10}$ is —C≡CH, —CH=$CH_2$, halogen, CN, $N_3$, $OR_{26}$, $OC(=O)R_{27}$, H, OH, $CH_3$ or $R_{10}$ forms a second bond between positions C-16 and C-17;

$R_{12}$ is H or forms a double bond with $R_1$ or $R_{14}$;

$R_{13}$ is halogen, $OR_{26}$, $OC(=O)R_{27}$, $NH_2$, $NHR_{26}$, NHC(=O)$R_{27}$, N($R_{26}$)$_2$, NC(=O)$R_{27}$, $N_3$, H, —OH, =O, —O—P(=O)(OH)$_2$, or —O—C(=O)—($CH_2$)$_t$COOH where t is an integer from 2 to 6;

$R_{14}$ is H or forms a double bond with $R_{12}$;

$R_{15}$ is H, =O or —OH;

and $R_{23}$ with $R_{10}$ forms a cyclic phosphate;

wherein $R_9$ and $R_{15}$ have the meaning defined above; or wherein $R_{23}$ is —OH, O—C(=O)—$R_{11}$, —OP(O)—(OH)$_2$, or —O—C(=O)—($CH_2$)$_t$COOH wherein t is an integer from 2 to 6; and $R_{11}$ is —Y—($CH_2$)$_n$—X—($CH_2$)$_m$—$SO_3H$, —Y'—($CH_2$)$_p$—X'—($CH_2$)$_q$—$NR_{16}R_{17}$ or —Z($CH_2$)$_r$Q, wherein Y is a bond or —O—; Y' is a bond, —O—, or —S—; each of X and X' is a bond, —CON($R_{18}$)—, —N($R_{18}$)CO—, —O—, —S—, —S(O)—, or —S($O_2$)—; $R_{18}$ is hydrogen or alkyl ($C_1$-$C_4$); each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocydic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —$R_{19}$—$CH_2COOH$ wherein $R_{19}$ is —S—, —S(O)—, —S(O)$_2$—, —$SO_2N(R_{20})$—, or N($R_{20}$)$SO_2$—; and $R_{20}$ is hydrogen or lower alkyl-($C_1$-$C_4$); with the proviso that the total number of carbon atoms in $R_{20}$ and ($CH_2$)$_r$ is not greater than 10; or (2) —CO—COOH; or (3) CON($R_{21}$)CH($R_{22}$)COOH wherein $R_{21}$ is H and $R_{22}$ is H, $CH_3$, —$CH_2COOH$, —$CH_2CH_2COOH$, —$CH_2OH$, —$CH_2SH$, —$CH_2CH_2SCH_3$, or —$CH_2Ph$—OH wherein Ph—OH is phydroxyphenyl;

or $R_{21}$ is $CH_3$ and $R_{22}$ is H;

or $R_{21}$ and $R_{22}$ taken together are —$CH_2CH_2CH_2$—;

or —N($R_{21}$)CH($R_{22}$)COOH taken together is —$NHCH_2CONHCH_2COOH$; and pharmaceutically acceptable salts thereof;

$R_{24}$=C, $C_1$-$C_2$ double bond, O;

$R_{25}$=C($R_{15}$)$CH_2$—$R_{23}$, OH, $OR_{26}$, OC(=O)$R_{27}$, $R_{26}$, COOH, C(=O)O$R_{26}$, $CHOHCH_2OH$, $CHOHCH_2OR_{26}$, $CHOHCH_2OC(=O)R_{27}$, $CH_2CH_2OHCH_2CH_2OR_{26}$, $CH_2CH_2OC(=O)R_{27}$, $CH_2CN$, $CH_2N_3$, $CH_2NH_2$, $CH_2NHR_{26}$, $CH_2N(R_{26})_2$, $CH_2OH$, $CH_2OR_{26}$, $CH_2O(C=O)R_{27}$, $CH_2O(P=O)(OH)_2$, $CH_2O(P=O)(OR_{26})_2$, $CH_2SH$, $CH_2S$—$R_{26}$, $CH_2SC(=O)R_{27}$, $CH_2NC(=O)R_{27}$, C(=O)$CHR_{28}OH$, C(=O)$CHR_{28}OR_{26}$, C(=O)$CHR_{28}OC(=O)R_{27}$ or $R_{10}$ and $R_{25}$ taken together may be =C($R_{28}$)$_2$, that is, an optionally alkyl substituted methylene group;

wherein $R_{26}$=$C_1$-$C_6$ (alkyl, branched alkyl, cydoalkyl, haloalkyl, aralkyl, aryl);

$R_{27}$=$R_{26}$+$OR_{26}$; $R_{28}$=H, $C_1$-$C_6$ (alkyl, branched alkyl, cycloalkyl) and at least one other IOP lowering compound selected from the group consisting of miotics, sympathomimetics, beta-blockers, carbonic anhydrase inhibitors, and prostagladins.

2. A composition for lowering IOP and controlling IOP spiking comprising a pharmaceutically effective amount of both 4,9(11)Pregnadien-17α,21-diol-3,20-dione-21-acetate and timolol.

3. A method for lowering IOP and controlling IOP spiking which comprises applying to an eye a pharmaceutically effective amount of an angiostatic agent with the structure Structure [A]

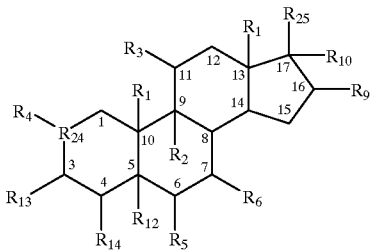

Structure [B]

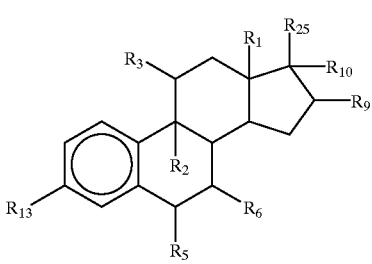

wherein $R_1$ is H, β—$CH_3$ or β—$C_2H_5$;

$R_2$ is F, $C_9$–$C_{11}$, double bond, $C_9$–$C_{11}$ epoxy, H or Cl;

$R_3$ is H, $OR_{26}$, $OC(=O)R_{27}$, halogen, $C_9$–$C_{11}$ double bond, $C_9$–Cl, epoxy, =O, —OH, —O— alkyl $(C_1-C_{12})$, —OC(=O)alkyl$(C_1-C_{12})$, —OC(=O)ARYL, —OC(=O)N(R)$_2$ or —OC(=O)$OR_7$ wherein ARYL is furyl, thienyl, pyrrolyl, or pyridyl and each of said moieties is optionally substituted with one or two $(C_1-C_4)$alkyl groups, or ARYL is —$(CH_2)_f$-phenyl wherein f is 0 to 2 and the phenyl ring is optionally substituted with 1 to 3 groups selected from chlorine, fluorine, bromine, alkyl$(C_1-C_3)$, alkoxy$(C_1-C_3)$, thioalkoxy-$(C_1-C_3)$, $Cl_3C$—, $F_3C$—, —$NH_2$ and —$NHCOCH_3$ and R is hydrogen, alkyl $(C_1-C_4)$, or phenyl and each R can be the same or different, and $R_7$ is ARYL as herein defined, or alkyl$(C_1-C_{12})$;

$R_4$ is H, $CH_3$, Cl or F;

$R_5$ is H, OH, F, Cl, Br, $CH_3$, phenyl, vinyl or allyl;

$R_6$ is H or $CH_3$;

$R_9$ is $CH_2CH_2OR_{26}$, $CH_2CH_2OC(=O)R_{27}$, H, OH, $CH_3$, F, =$CH_2$, $CH_2C(=O)OR_{28}$, $OR_{26}$, $O(C=O)R_{27}$ or $O(C=O)CH_2C(=O)OR_{26}$ $R_{10}$ is —C≡CH, —CH=$CH_2$, halogen, CN, $N_3$, $OR_{26}$, $OC(=O)R_{27}$, H, OH, $CH_3$ or $R_{10}$ forms a second bond between positions C-16 and C-17;

$R_{12}$ is H or forms a double bond with $R_1$ or $R_{14}$;

$R_{13}$ is halogen, $OR_{26}$, $OC(=O)R_{27}$, $NH_2$, $NHR_{26}$, NHC(=O)$R_{27}$, N(R$_{26}$)$_2$, NC(=O)$R_{27}$, $N_3$, H, —OH, =O, —O—P(=O)(OH)$_2$, or —O—C(=O)—(CH$_2$)$_t$COOH where t is an integer from 2 to 6;

$R_{14}$ is H or forms a double bond with $R_{12}$;

$R_{15}$ is H, =O or —OH;

and $R_{23}$ with $R_{10}$ forms a cyclic phosphate;

wherein $R_9$ and $R_{15}$ have the meaning defined above;

or wherein $R_{23}$ is —OH, O—C(=O)—$R_{11}$, —OP(O)(OH)$_2$, or —O—C(=O)—(CH$_2$)$_t$COOH wherein t is an integer from 2 to 6; and $R_{11}$ is —Y—(CH$_2$)$_n$—X—(CH$_2$)$_m$—SO$_3$H, —Y'—(CH$_2$)$_p$—X'—(CH$_2$)$_q$—NR$_{16}$R$_{17}$ or —Z(CH$_2$)$_r$Q, wherein Y is a bond or —O—; Y' is a bond, —O—, or —S—; each of X and X' is a bond, —CON(R$_{18}$)—, —N(R$_{18}$)CO—, —O—, —S—, —S(O)—, or —S(O$_2$)—; $R_{18}$ is hydrogen or alkyl $(C_1-C_4)$; each of $R_{16}$ and $R_{17}$ is a lower alkyl group of from 1 to 4 carbon atoms optionally substituted with one hydroxyl or $R_{16}$ and $R_{17}$ taken together with the nitrogen atom to which each is attached forms a monocydic heterocycle selected from pyrrolidino, piperidino, morpholino, thiomorpholino, piperazino or N(lower)alkyl-piperazino wherein alkyl has from 1 to 4 carbon atoms; n is an integer of from 4 to 9; m is an integer of from 1 to 5; p is an integer of from 2 to 9; q is an integer of from 1 to 5;

Z is a bond or —O—; r is an integer of from 2 to 9; and Q is one of the following:

(1) —$R_{19}$—$CH_2COOH$ wherein $R_{19}$ is —S—, —S(O)—, —S(O)$_2$—, —SO$_2$N(R$_{20}$)—, or N(R$_{20}$)SO$_2$—; and $R_{20}$ is hydrogen or lower alkyl-$(C_1-C_4)$; with the proviso that the total number of carbon atoms in $R_{20}$ and (CH$_2$)$_r$ is not greater than 10; or (2) —CO—COOH; or (3) CON(R$_{21}$)CH(R$_{22}$)COOH wherein $R_{21}$ is H and $R_{22}$ is H, $CH_3$, —$CH_2COOH$, —$CH_2CH_2COOH$, —$CH_2OH$, —$CH_2SH$, —$CH_2CH_2SCH_3$, or —$CH_2Ph$—OH wherein Ph—OH is phydroxyphenyl;

or $R_{21}$ is $CH_3$ and $R_{22}$ is H;

or $R_{21}$ and $R_{22}$ taken together are —$CH_2CH_2CH_2$—;

or —N(R$_{21}$)CH(R$_{22}$)COOH taken together is —NHCH$_2$CONHCH$_2$COOH; and pharmaceutically acceptable salts thereof;

$R_{24}$=C, $C_1$-$C_2$ double bond, O;

$R_{25}$=C(R$_{15}$)CH$_2$—R$_{23}$, OH, OR$_{26}$, OC(=O)R$_{27}$, R$_{26}$, COOH, C(=O)OR$_{26}$, CHOHCH$_2$OH, CHOHCH$_2$OR$_{26}$, CHOHCH$_2$OC(=O)R$_{27}$, CH$_2$CH$_2$OHCH$_2$CH$_2$OR$_{26}$, CH$_2$CH$_2$OC(=O)R$_{27}$, CH$_2$CN, CH$_2$N$_3$, CH$_2$NH$_2$, CH$_2$NHR$_{26}$, CH$_2$N(R$_{26}$)$_2$, CH$_2$OH, CH$_2$OR$_{26}$, CH$_2$O(C=O)R$_{27}$, CH$_2$O(P=O)(OH)$_2$, CH$_2$O(P=O) (OR$_{26}$)$_2$, CH$_2$SH, CH$_2$S—R$_{26}$, CH$_2$SC(=O)R$_{27}$, CH$_2$NC(=O)R$_{27}$, C(=O)CHR$_{28}$OH, C(=O)CHR$_{28}$OR$_{26}$, C(=O)CHR$_{28}$OC(=O)R$_{27}$ or $R_{10}$ and $R_{25}$ taken together may be =C(R$_{28}$)$_2$, that is, an optionally alkyl substituted methylene group;

wherein $R_{26}$=$C_1$-$C_6$ (alkyl, branched alkyl, cydoalkyl, haloalkyl, aralkyl, aryl);

$R_{27}$=$R_{26}$+OR$_{26}$; $R_{28}$=H, $C_1$-$C_6$ (alkyl, branched alkyl, cycloalkyl) and at least one other IOP lowering compound selected from the group consisting of miotics, sympathomimetics, beta-blockers, carbonic anhydrase inhibitors, and prostagladins.

4. A method for lowering IOP and controlling IOP spiking which comprises administering to an affected eye, a composition comprising a pharmaceutically effective amount of both 4,9(11)Pregnadien-17α,21-diol-3,20-dione-21-acetate and timolol.

5. The composition of claim 1 wherein the angiostatic agent is 4,9(11)Pregnadien-17α,21-diol-3,20-dione-21-acetate and the other IOP lowering compound is a beta-blocker.

6. The composition of claim 1 wherein the angiostatic agent is 4,9(11)Pregnadien-17α,21-diol-3,20-dione-21-acetate and the other IOP lowering compound is a miotic.

7. The composition of claim 1 wherein the angiostatic agent is 4,9(1)Pregnadien-17α,21-diol-3,20-dione-21-acetate and the other IOP lowering compound is a sympathomimetic.

8. The composition of claim 1 wherein the angiostatic agent is 4,9(1 )Pregnadien-17α,21-diol-3,20-dione-21-acetate and the other IOP lowering compound is a carbonic anhydrase inhibitor.

9. The composition of claim 1 wherein the angiostatic agent is 4,9(11)Pregnadien-17α,21-diol-3,20-dione-21-acetate and the other IOP lowering compound is a prostaglandin.

10. The method of claim 3 wherein the angiostatic agent is 4,9(11)Pregnadien-17α,21-diol-3,20-dione-21-acetate and the other IOP lowering compound is a beta-blocker.

11. The method of claim 3 wherein the angiostatic agent is 4,9(11)Pregnadien-17α,21-diol-3,20-dione-21-acetate and the other IOP lowering compound is a miotic.

12. The method of claim 3 wherein the angiostatic agent is 4,9(11)Pregnadien-17α,21-diol-3,20-dione-21-acetate and the other IOP lowering compound is a sympathomimetic.

13. The method of claim 3 wherein the angiostatic agent is 4,9(11)Pregnadien-17α,21-diol-3,20-dione-21-acetate and the other IOP lowering compound is a carbonic anhydrase inhibitor.

14. The method of claim 3 wherein the angiostatic agent is 4,9(11 )Pregnadien-17α,21-diol-3,20-dione-21-acetate and the other IOP lowering compound is a prostaglandin.

15. A composition for lowering IOP and controlling IOP spiking comprising a pharmaceutically effective amount of both 4,9(11 )Pregnadien-17α,21-diol-3,20-dione-21-acetate and betaxolol.

16. A method for lowering IOP and controlling IOP spiking which comprises administering to an affected eye, a composition comprising a pharmaceutically effective amount of both 4,9(11 )Pregnadien-17α,21-diol-3,20-dione-21-acetate and betaxolol.

* * * * *